United States Patent [19]
Lattin et al.

[11] Patent Number: 5,843,014
[45] Date of Patent: Dec. 1, 1998

[54] DISPLAY FOR AN ELECTROTRANSPORT DELIVERY DEVICE

[75] Inventors: Gary A. Lattin, Forest Lake, Minn.; Keith J. Bernstein, Somerville, N.J.

[73] Assignee: ALZA Corporation, Palo Alto, Calif.

[21] Appl. No.: 410,112

[22] Filed: Mar. 24, 1995

[51] Int. Cl.$^6$ .................................................. A61N 1/30
[52] U.S. Cl. ............................................. 604/20; 604/49
[58] Field of Search ......................................... 604/20, 49

[56] References Cited

U.S. PATENT DOCUMENTS

| | | |
|---|---|---|
| 4,141,359 | 2/1979 | Jacobsen et al. . |
| 4,474,570 | 10/1984 | Ariura et al. . |
| 4,588,580 | 5/1986 | Gale et al. . |
| 4,927,408 | 5/1990 | Haak et al. . |
| 5,006,108 | 4/1991 | LaPrade . |
| 5,047,007 | 9/1991 | McNichols et al. . |
| 5,203,768 | 4/1993 | Haak et al. . |
| 5,224,927 | 7/1993 | Tapper . |
| 5,224,928 | 7/1993 | Sibalis et al. . |
| 5,232,438 | 8/1993 | Theeuwes et al. . |
| 5,232,448 | 8/1993 | Zdeb . |
| 5,246,418 | 9/1993 | Haynes et al. . |
| 5,254,081 | 10/1993 | Maurer et al. . |

FOREIGN PATENT DOCUMENTS

| | | | |
|---|---|---|---|
| 0060452 | 9/1982 | European Pat. Off. .......... | A61N 1/24 |
| 0461680 | 12/1991 | WIPO .............................. | A61N 1/24 |
| WO9303790 | 4/1993 | WIPO .............................. | A61N 1/24 |

OTHER PUBLICATIONS

S. Thysman et al., "Transdermal Iontophoresis of Fentanyl: Delivery and Mechanistic Analysis," *International Journal of Pharmaceutics*, 101 (1994) 105–113.

V. Préat et al., "Transdermal Iontophoretic Delivery of Sufentanil," 96 *International Journal of Pharmaceutics*, 189–196 (1993).

M. Ashburn et al., "Iontophoretic Delivery of Morphine for Postoperative Analgesia," vol. 7, No. 1, *Journal of Pain and Symptom Management*, 27–33, 1992.

Gourlav et al., "The Transdermal Administration of Fentanyl in the Treatment of Postoperative Pain Pharmacokinetics and Pharmacodynamic Effects," *Pain*, 1989; 37:193–202.

Sebel et al., "Transdermal Absorption of Fentanyl and Sufentanil in Man," 32 *Eur. J. Clin. Pharmacal*, 529–531 (1987).

Barkas et al., "Advances in Cancer Pain Management: A Review of Patient–Controlled Analgesia," vol. 3, No. 3, *Journal of Pain and Symptom Management*, 150–160 (1988).

White, Paul F., "Patient–Controlled Analgesia: Delivery Systems," 70–81.

Thysman et al., "In Vivo Iontophoresis of Fentanyl and Sufentanil in Rats: Pharmacokinetics and Acute Antinociceptive Effects," *Anesth Analg*, 61–66 (1993).

*Primary Examiner*—Mark Bockelman
*Attorney, Agent, or Firm*—D. Byron Miller; Steve F. Stone

[57] ABSTRACT

An electrotransport delivery device (10) with a display (14) having only on and off states, and a method of operating the display (14), are provided. Preferably, the display 14 is a light (e.g., a light emitting diode) with lit and unlit states or an audible alarm (e.g., a beeper) with sounding and silent states. The device (10) counts and stores the number of events (e.g., patient initiated drug delivery or sensed patient condition) which occur over a predetermined period of time (e.g., the period of time over which the device is worn by the patient). The event count is displayed by cycling the display (14) between on and off states according to a predetermined regimen which correlates the number of on/off cycles to the number of events. The device and method permit the use of a simple and inexpensive means (e.g., an LED) to display (e.g., to a medical technician) the number of e.g., patient initiated doses delivered over a previous period of therapy.

29 Claims, 4 Drawing Sheets

DISPLAY FOR AN ELECTROTRANSPORT DELIVERY DEVICE

TECHNICAL FIELD

The present invention relates to delivery of drug or agent through an intact body surface, such as skin, by electrotransport. Yet more specifically, the present invention relates to an electrotransport drug delivery device with an inexpensive display for displaying the number of events which have occurred over a preceding period of therapy.

BACKGROUND ART

Recently, much attention in the patent and technical literature has been directed to delivery of drug or agent through intact skin or organ surfaces by electrotransport. The term "electrotransport" as used herein refers generally to the delivery of a beneficial agent (e.g., a drug) through a biological membrane, such as skin, mucous membranes, or nails. The delivery is induced or aided by application of an electrical potential. For example, a beneficial therapeutic agent may be introduced into the systemic circulation of a human body by electrotransport delivery through the skin. A widely used electrotransport process, electromigration (also called iontophoresis), involves the electrically induced transport of charged ions. Another type of electrotransport, electroosmosis, involves the flow of a liquid containing the agent to be delivered, under the influence of an electric field. Still another type of electrotransport process, electroporation, involves the formation of transiently-existing pores in a biological membrane by the application of an electric field. An agent can be delivered through the pores either passively (i.e., without electrical assistance) or actively (i.e., under the influence of an electric potential). However, in any given electrotransport process, more than one of these processes may be simultaneously occurring. Accordingly, the term "electrotransport", as used herein, should be given its broadest possible interpretation so that it includes the electrically induced or enhanced transport of at least one agent, which may be charged, uncharged, or a mixture of charged and uncharged species, regardless of the specific mechanism or mechanisms by which the agent actually is transported.

Electrotransport devices use at least two electrodes that are in electrical contact with some portion of the skin, nails, mucous membranes, organ surfaces, or other surface of the body. One electrode, commonly called the "donor" or "active" electrode, is the electrode from which the agent is delivered into the body. The other electrode, typically termed the "counter" or "return" electrode, serves to close the electrical circuit through the body. For example, if the agent to be delivered is positively charged, i.e., a cation, then the anode is the active or donor electrode, while the cathode serves to complete the circuit. Alternatively, if an agent is negatively charged, i.e., an anion, the cathode is the donor electrode. Additionally, both the anode and cathode may be considered donor electrodes if both anionic and cationic agent ions, or if uncharged dissolved agents, are to be delivered.

Furthermore, electrotransport delivery systems generally require at least one reservoir which contains a liquid solution or suspension of the agent to be delivered to the body. Examples of such donor reservoirs include a pouch or cavity, a porous sponge or pad, and a hydrophilic polymer or a gel matrix. Such donor reservoirs are electrically connected to, and positioned between, the anode or cathode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. In addition, some electrotransport devices have an electrical controller that controls the current applied through the electrodes, thereby regulating the rate of agent delivery. Furthermore, passive flux control membranes, adhesives for maintaining device contact with a body surface, insulating members, and impermeable backing members are some other potential components of an electrotransport device.

All electrotransport agent delivery devices utilize an electrical circuit to electrically connect the power source (e.g., a battery) and the electrodes. In very simple devices, such as those disclosed in Ariura et al. U.S. Pat. No. 4,474,570, the "circuit" is merely an electrically conductive wire used to connect the battery to an electrode. Other devices use a variety of electrical components to control the amplitude, polarity, timing, waveform shape, etc. of the electric current supplied by the power source. See, for example, McNichols et al. U.S. Pat. No. 5,047,007.

To date, commercial transdermal electrotransport drug delivery devices (e.g., the Phoresor, sold by Iomed, Inc. of Salt Lake City, Utah; the Dupel Iontophoresis System sold by Empi, Inc. of St. Paul, Minn.; the Webster Sweat Inducer, model 3600, sold by Wescor, Inc. of Logan, Utah) have generally utilized a desk-top electrical power supply unit and a pair of skin contacting electrodes. The donor electrode contains a drug solution while the counter electrode contains a solution of a bio-compatible electrolyte salt. The "satellite" electrodes are connected to the electrical power supply unit by long (e.g., 1–2 meters) electrically conductive wires or cables. Examples of desk-top electrical power supply units which use "satellite" electrode assemblies are disclosed in Jacobsen et al. U.S. Pat. No. 4,141,359 (see FIGS. 3 and 4); LaPrade U.S. Pat. No. 5,006,108 (see FIG. 9); and Maurer et al. U.S. Pat. No. 5,254,081 (see FIGS. 1 and 2).

More recently, small, self-contained electrotransport delivery devices, adapted to be worn on the skin for extended periods of time, have been proposed. The electrical components of such miniaturized electrotransport drug delivery devices are also preferably miniaturized, and may be in the form of either integrated circuits (i.e., microchips) or small printed circuits. Electronic components, such as batteries, resistors, pulse generators, capacitors, etc., are electrically connected to form an electronic circuit that controls the amplitude, polarity, timing, waveform shape (and other parameters) of the electric current supplied by the power source. Such small self-contained electrotransport delivery devices are disclosed, for example, in Tapper U.S. Pat. No. 5,224,927; Haak et al. U.S. Pat. No. 5,203,768; Sibalis et al. U.S. Pat. No. 5,224,928; and Haynes et al. U.S. Pat. No. 5,246,418.

Drug delivery pumps which allow a patient to determine when, and how frequently, to self administer a drug are known and used. Such devices are used particularly in treating pain using analgesics. Analgesics, i.e., drugs or agents that reduce or eliminate pain, are often prescribed to relieve pain, such as post-operative pain or chronic pain associated with certain types of cancer. Especially with respect to post-operative pain, difficulty has been encountered in analgesic administration. The difficulty has been in achieving the desired mitigation or elimination of pain without the over (or under) utilization of the analgesic. This difficulty in properly administering analgesics originates from a variety of factors. The patient's age, hepatic function, renal function, and the interaction between the administered analgesic and other medication(s) being taken by the patient can all affect the pharmacokinetics of analgesics and thereby affect the patient's need for such analgesic. Because of the patient-to-patient variability in the therapeutically effective dose, certain patients continue to suffer even after conventional dosages of analgesics have been administered. Further, there is a tendency for doctors and nurses to under-prescribe and to under-administer narcotic analgesics for fear that a patient may become addicted to them or that a patient may suffer serious side-effects (e.g., respiratory depression) as a result of over-dosing.

More recently, considerable attention has been given to devices and systems which permit, within predetermined limits, the patient to control the amount of analgesic the patient receives. The experience has generally been that patient control of the administration of analgesic has resulted in the administration of less analgesic to the patient than would have been administered were the dosage prescribed by the physician. Self-administration or patient controlled self-administration of analgesic drugs has become known (and will be referred to herein) as patient-controlled analgesia (PCA).

Known PCA devices are typically electromechanical pumps which require large capacity electrical power sources, e.g., alternating current or multiple large capacity battery packs which are bulky. Due to their bulk and complexity, such commercially available devices generally require the patient to be confined to a bed, or some other essentially fixed location.

PCA devices deliver drug to the patient by means of an intravenously or subcutaneously positioned line or a catheter. Such structures must be inserted into the intended vessel or tissue by a qualified medical technician. This technique requires that the skin barrier be breached which creates a risk of infection. (See, Zdeb U.S. Pat. No. 5,232,448). Thus, as practiced using commercially available PCA devices, PCA requires the presence of skilled medical technicians to initiate and supervise the operation of the PCA device along with its attendant risk of infection. Further, commercially available PCA devices themselves are somewhat painful to use by virtue of their percutaneous (i.e., intravenous or subcutaneous) access.

Transdermal delivery of narcotic analgesic drugs, such as fentanyl, by both passive diffusion and electrically-assisted delivery in order to induce analgesia, have been described in the patent literature. See, for example Gale et al. U.S. Pat. No. 4,588,580, and Theeuwes et al, U.S. Pat. No. 5,232,438. Transdermal delivery of fentanyl by electrotransport (specifically iontophoresis) has been described in the technical literature by S. Thysman et al. in "Transdermal Iontophoresis of Fentanyl: Delivery and Mechanistic Analysis", *International Journal of Pharmaceutics*, 101 (1994) 105–113. Thysman et al. compared in vitro transdermal iontophoretic delivery of fentanyl (through excised rat skin using a plexiglass cell) with in vitro passive transdermal delivery of fentanyl. Thysman et al. concluded that iontophoresis improved the pharmacokinetic profile for the transdermal administration of fentanyl.

V. Préat et al. also describe the electrotransport delivery of sufentanil, an analog of fentanyl, in "Transdermal Iontophoretic Delivery of Sufentanil", 96 *International Journal of Pharmaceutics*, 189–196 (1993).

M. Ashburn et al. describe iontophoretic delivery of morphine in conjunction with morphine delivery by means of a conventional PCA device in "Iontophoretic Delivery of Morphine for Postoperative Analgesia" Vol. 7, No. 1, *Journal of Pain and Symptom Management*, 27–33, 1992. Ashburn et al. concluded that iontophoretic delivery of morphine reduced the utilization of conventional PCA in postoperative pain management. See also, Gourlav et al. "The Transdermal Administration of Fentanyl in the Treatment of Postoperative Pain Pharmacokinetics and Pharmacodynamic Effects", *Pain*, 1989; 37:193–202; Sebel et al. "Transdermal Absorption of Fentanyl and Sufentanil in Man", 32 Eur. J. Clin. Pharmacal 529–531 (1987).

In the administration of drugs such as analgesics, it is very desirable for attending medical personnel to have knowledge regarding the history of the patient's receipt of drug. For example, in pain management, information regarding the amount of analgesic received by the patient during a given prior period of time (i.e., dosage history), can be critically important in deciding upon a future strategy to be used to manage a patient's pain or other symptoms. It is also important that an electrotransport patient-controlled drug delivery device be easy for both the patient and medical professionals to use.

DISCLOSURE OF THE INVENTION

The present invention provides an electrotransport drug delivery device and method which provides storage and display of prior events which have occurred over the course of therapy.

It is a further aspect of the present invention to provide a display for an electrotransport drug delivery device, which is inexpensive, which is accurate, and easy for both medical professionals and patients to use.

It is a preferred aspect of the present invention to provide a patient-controlled electrotransport drug delivery device and method which records and displays, for interpretation by medical professionals, the number of doses of drug the patient has self-administered during a predeterminable prior time period. Knowing the number of prior drug delivery events, medical professionals can easily determine (or look up) such derived or derivable quantities as total drug delivered, undelivered drug remaining in the drug reservoir, drug delivery trends (i.e., increasing or decreasing) and various other data relating to the patient's drug delivery profile.

The present invention provides a method and device for displaying how many events have occurred over a period of use of a patient-worn electrotransport delivery device. The delivery device utilizes a display having on and off states. The method includes counting and storing the number of events which occur over the period of use. The stored count is displayed by cycling the display between on and off states according to a predetermined regimen which correlates the number of on/off cycles to the stored count. Preferably, the predetermined regimen correlates each on/off cycle of the display to between x and y events, x and y each being an integer from 0 to 100, more preferably an integer from 1 to 20.

The display is preferably an inexpensive display such as a light having lit and unlit states or an audible alarm having sounding and no-sounding states.

The events which are counted can be doses of drug delivered by the device by electrotransport. Alternatively, the events may comprise a patient condition which is sensed by the device. The sensed condition may be compared with a predetermined range for that condition and counted each time the condition falls outside the predetermined range. In a more preferred practice of the invention, the event is a manually initiated dose of drug administered by electrotransport.

These and other objects and advantages of the present invention will become apparent from the following detailed description of the invention and from the accompanying drawings.

BRIEF DESCRIPTION OF THE DRAWINGS

In the figures, like parts are given like reference numerals and wherein.

MODES FOR CARRYING OUT THE INVENTION

Figure 1:
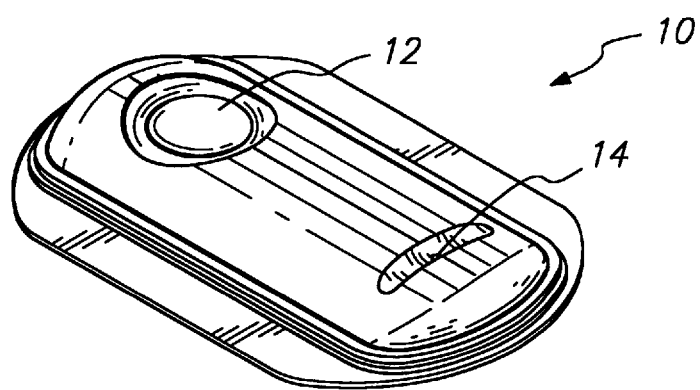
FIG. 1 is a perspective view of an electrotransport drug delivery device of this invention.

Generally speaking, the electrotransport device of this invention can be used by patients to deliver substantially any drug during a prescribed course of therapy. One specific and preferred example of an event and a course of therapy is the delivery of a drug (e.g., an analgesic) to control pain. Drug is self-administered by the patient by closing a switch which activates the electrotransport device. Once activated, the device delivers drug by electrotransport for a predetermined delivery interval. Thus, in this example of the invention, the event is a predetermined dose of drug delivered automatically upon activation of the device. The length of the delivery interval will vary depending upon the particular drug being delivered, the magnitude of the applied current, the size of the device and the particular course of therapy. After the delivery interval expires, the device automatically turns itself off and awaits activation to deliver another dose of drug. If the patient needs more drug, e.g., if the patient is continuing to feel pain after the delivery interval has expired, the activation switch may be again closed and the device placed in a drug delivery mode for another predetermined delivery interval. On the other hand, if the patient has adequate pain relief following the drug delivery interval, the device automatically shuts itself off and awaits another activation by the patient at a later time when pain reappears. The patient is thus able to titrate the drug to his or her level of pain tolerance (within definable limits) to achieve a desired level of analgesia, i.e., where the patient is not uncomfortable. The device is designed to be worn on the patient's skin (e.g., upper arm, lower arm, or chest) for a predetermined period of therapy e.g., 24-hours. The device can then be discarded or returned to the physician as directed.

In accordance with the present invention, the device has a display, in the form of a light or an audible alarm, with only on and off states. Examples of such displays include simple lights, LED's and beepers which are generally inexpensive and thus well adapted for use in electrotransport devices which are completely disposable.

The electrotransport device of the present invention also includes an electronic counter and storage apparatus for counting and storing the number of events e.g., the number of times that the device is activated to deliver a dose of drug. Thus, the counter and storage apparatus is operatively connected to the activation switch such that the counter is incremented by one every time the switch is closed and the device is activated.

The display is also operationally connected to the counter and storage apparatus to display the stored count (e.g., the number of times that the device has been activated to deliver a dose of drug). The display displays the count by cycling between on and off states according to a predetermined regimen which correlates the number of on/off cycles to the count. Preferably, the predetermined regimen correlates each on/off cycle of the display to between x and y events (e.g., doses), x and y each being an integer from 0 to 100, more preferably an integer from 1 to 20 and most preferably an integer from 1 to 10. In this manner, the dosing history (i.e., the number of doses of drug administered by the patient) is displayed, at least to an approximate number, by the cycling of the display between on and off states (e.g., by blinking a light or by sounding an audible alarm) according to the predetermined regimen. Thus, a single light can be used to display the number of events which have previously occurred during the course of therapy.

While the present invention is not limited to electrotransport delivery of any particular drug or to any particular course of therapy, the device and method of the present invention has particular utility in connection with manually initiated electrotransport drug delivery and more particularly manually initiated electrotransport delivery of an analgesic drug to control pain. Examples of electrotransport delivery devices adapted to deliver a narcotic analgesic on demand by the patient in order to control pain are illustrated in FIGS. 1–4. With reference to FIG. 1, there is shown a perspective view of an electrotransport device 10 having an activation switch in the form of a push button switch 12 and a display in the form of a light emitting diode (LED) 14. In view of the description hereinafter, various other structures which operate in a similar manner to the switch 12 and the LED 14 will become readily apparent to one skilled in this art.

Figure 2:
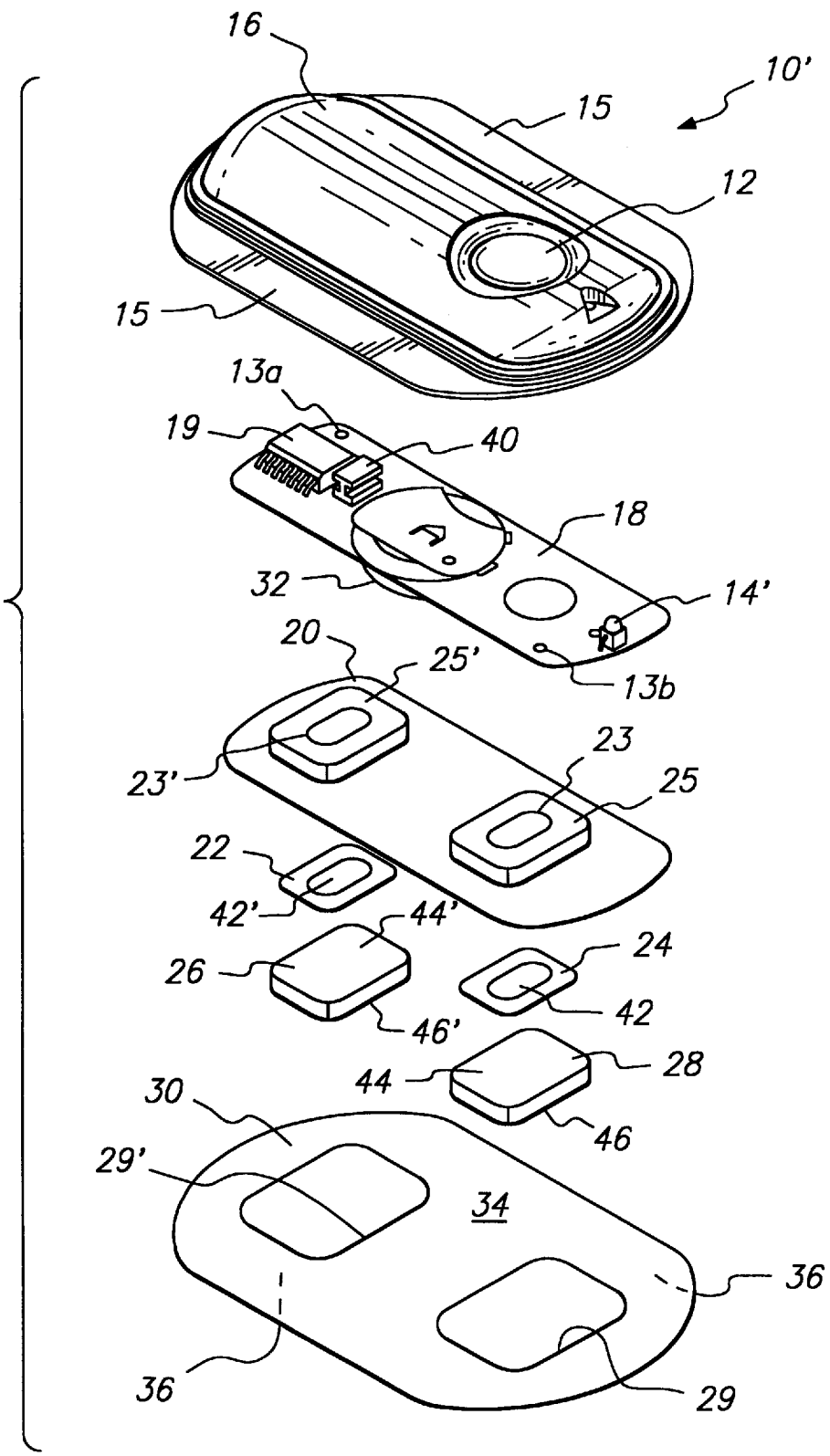
FIG. 2 is an exploded view of an electrotransport device of this invention.

FIG. 2 is an exploded view of a second device 10' of this invention. The device 10' of FIG. 2 differs from device 10 of FIG. 1 in the location of LED 14'. LED 14' is located adjacent button switch 12 on one end of device 10' in this embodiment of the invention. Device 10' comprises an upper housing 16, a circuit board assembly 18, a lower housing 20, anode electrode 22, cathode electrode 24, anode reservoir 26, cathode reservoir 28 and skin-compatible adhesive 30. Upper housing 16 has lateral wings 15 which assist in holding device 10' on a patient's skin. Upper housing 16 is preferably composed of an injection moldable elastomer (e.g., ethylene vinyl acetate). Printed circuit board assembly 18 comprises an integrated circuit 19 coupled to discrete components 40 and battery 32. Circuit board assembly 18 is attached to housing 16 by posts (not shown in FIG. 2) passing through openings 13a and 13b, the ends of the posts being heated/melted in order to heat stake the circuit board assembly 18 to the housing 16. Lower housing 20 is attached to the upper housing 16 by means of adhesive 30, the upper surface 34 of adhesive 30 being adhered to both lower housing 20 and upper housing 16 including the bottom surfaces of wings 15.

Shown (partially) on the underside of circuit board assembly 18 is a button cell battery 32. Other types of batteries may also be employed to power device 10'.

The device 10' is generally comprised of battery 32, electronic circuitry 19,40, electrodes 22,24, and drug/chemical reservoirs 26,28, all of which are integrated into a self-contained unit. The outputs (not shown in FIG. 2) of the circuit board assembly 18 make electrical contact with the electrodes 24 and 22 through openings 23,23' in the depressions 25,25' formed in lower housing 20, by means of electrically conductive adhesive strips 42,42'. Electrodes 22 and 24, in turn, are in direct mechanical and electrical contact with the top sides 44',44 of drug reservoirs 26 and 28. The bottom sides 46',46 of drug reservoirs 26,28 contact the patient's skin through the openings 29',29 in adhesive 30.

Upon depression of push button switch 12, the electronic circuitry on circuit board assembly 18 delivers a predetermined DC current to the electrode/reservoirs 22,26 and 24,28 for a delivery interval of predetermined length, e.g., about 10 minutes. Preferably, the device transmits to the user a visual and/or audible confirmation of the onset of the drug delivery, or bolus, interval by means of LED 14' becoming lit and/or an audible sound signal from, e.g., a "beeper". Drug is delivered through the patient's skin by electrotransport, e.g., on the arm, for the ten minute period, each ten minute period being a single dose or drug delivery event. The circuitry on circuit board assembly 18 includes an electrical component, e.g., a counter, which counts the number of delivery events and stores that information in a register.

Anodic electrode 22 is preferably comprised of silver and cathodic electrode 24 is preferably comprised of silver chloride. Both reservoirs 26 and 28 are preferably comprised of polymer hydrogel materials. Electrodes 22,24 and reservoirs 26,28 are retained by lower housing 20. While the invention is not limited to any particular drug reservoir composition or electrode material, the invention has particular utility in the delivery of analgesics. One particularly suitable analgesic is fentanyl, preferably a hydrochloride or citrate salt of fentanyl. In the case of fentanyl HCl, the anodic reservoir 26 is the "donor" reservoir and contains the fentanyl HCl and the cathodic reservoir 28 contains a biocompatible electrolyte.

The push button switch 12, the electronic circuitry on circuit board assembly 18 and the battery 32 are adhesively "sealed" between upper housing 16 and lower housing 20. Upper Housing 16 is preferably composed of rubber or other elastomeric material. Lower housing 20 is preferably composed of a plastic or elastomeric sheet material (e.g., polyethylene) which can be easily molded to form depressions 25,25' and cut to form openings 23,23'. The assembled device 10' is preferably water resistant (i.e., splash proof) and is most preferably waterproof. The system has a low profile that easily conforms to the body thereby allowing freedom of movement at, and around, the wearing site. The anode/fentanyl reservoir 26 and the cathode/salt reservoir 28 are located on the skin-contacting side of the device 10' and are sufficiently separated to prevent accidental electrical shorting during normal handling and use.

The device 10' adheres to the patient's body surface (e.g., skin) by means of a peripheral adhesive 30 which has upper side 34 and body-contacting side 36. The adhesive side 36 has adhesive properties which assures that the device 10' remains in place on the body during normal user activity, and yet permits reasonable removal after the predetermined (e.g., 24-hour) wear period. Upper adhesive side 34 adheres to lower housing 20 and retains the electrodes and drug reservoirs within housing depression 25, 25' as well as retains lower housing 20 attached to upper housing 16.

The push button switch 12 is conveniently located on the top side of device 10' and is easily actuated through clothing. A double press of the push button switch 12 within a short time period, e.g., three seconds, is preferably used to activate the device for delivery of drug, thereby minimizing the likelihood of inadvertent actuation of the device 10'.

Upon switch activation an audible alarm signals the start of drug delivery, at which time the circuit supplies a predetermined level of DC current to the electrodes/reservoirs for a predetermined delivery interval. In the case of electrotransporting fentanyl to control acute pain, the applied current is typically in the range of about 10 to 5000 $\mu$A, preferably about 50 to 500 $\mu$A and most preferably about 200 to 300 $\mu$A. In the case of electrotransporting fentanyl to control acute pain, the delivery interval is typically in the range of about 1 to 120 minutes, preferably about 5 to 30 minutes and most preferably about 10 minutes. The LED 14' remains "on" throughout the delivery interval indicating that the device 10' is in an active drug delivery mode. The battery 32 preferably has sufficient capacity to continuously power the device 10' at the predetermined level of DC current for the entire predetermined (e.g., 24-hour) wearing period.

In a preferred practice of this invention, a small, light weight and inexpensive light with on and off (i.e., lit and unlit) states is used as the display. In a more preferred practice of the invention, the display is an LED.

Preferably, the drug delivery history information is displayed automatically by blinking the LED on and off according to the predetermined regimen. In the case of an electrotransport delivery device having both "on" and "off" modes, the LED most preferably (i) displays the event count (e.g., dosing history) only when the device is in an "off" mode and (ii) is in a continually lit state during the drug delivery interval in order to signal on-going drug delivery.

Figure 4:
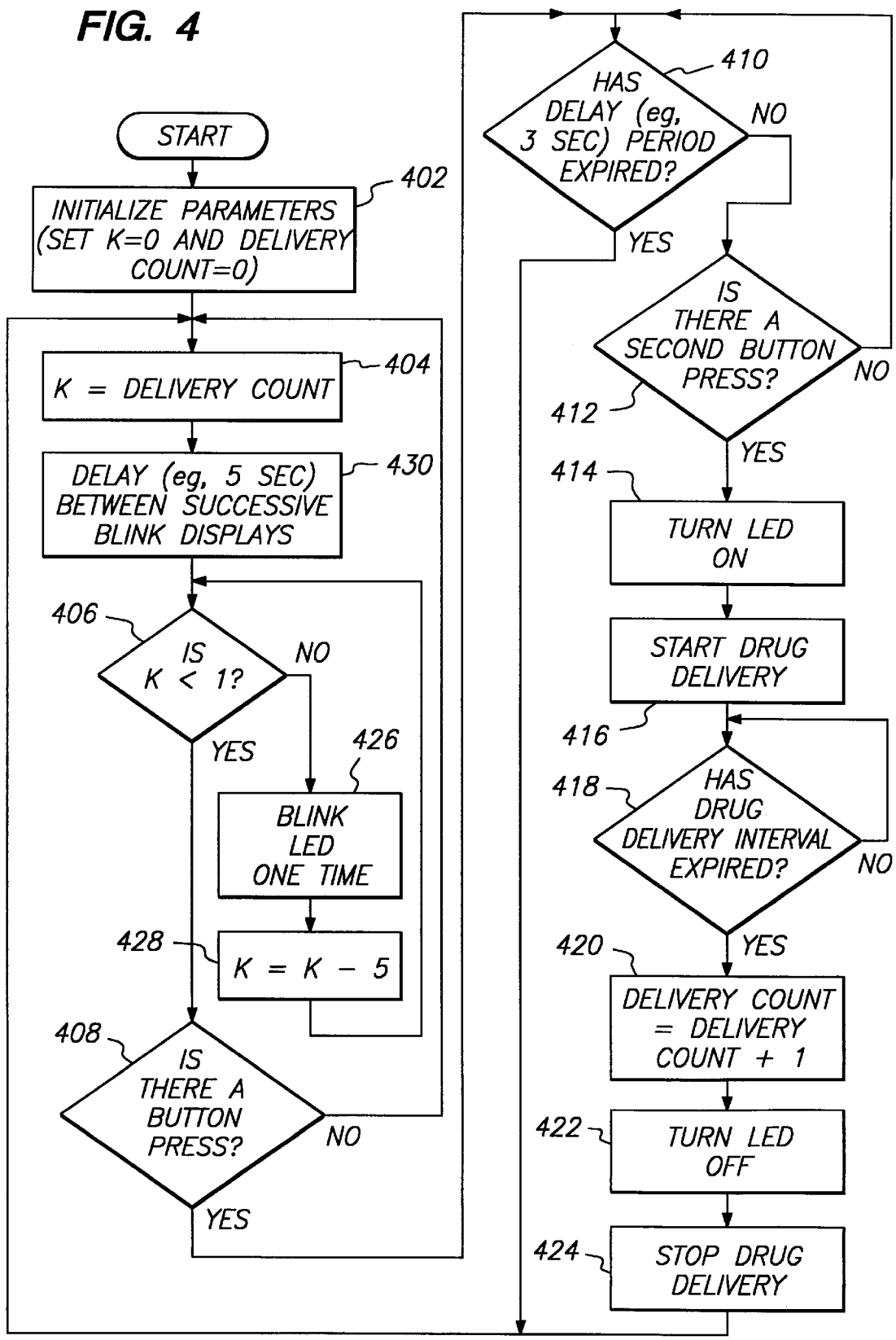
FIG. 4 is a flow diagram showing an alternative logic of operation for the device illustrated in FIG. 2.

FIG. 4 is a flow diagram showing the mode of operation wherein the event count is displayed automatically by blinking the LED on and off when the delivery device is in an "off" mode (i.e., during times other than drug delivery intervals). The placement of the device upon the patient closes the electrical circuit between the donor and counter electrode assemblies of the device. The operations illustrated in FIG. 4 may be initiated by manually depressing push button switch 12 or by the device automatically electronically sensing its placement upon the patient's skin. The first step (boxes 402 and 404) is to initialize certain parameters, including setting a variable K equal to zero and then setting the drug delivery count equal to K, or zero. The delivery count is the stored number of drug delivery events (i.e., the number of times that the device has been activated to deliver drug). Since K is initially set equal to zero, the answer to the question posed in box 406 is "yes" and the logic of the flow diagram cycles between boxes 406 and 408 until the button switch 12 is pressed. Once button switch 12 is pressed, the answer to the question posed in box 408 is "yes" and the logic of the flow diagram cycles between boxes 410 and 412 until the short (e.g., 3 second) delay period has expired or until there is a second press of button switch 12, whichever occurs first. If the 3 second delay period expires before button switch 12 is pressed a second time, the answer to the question posed in box 410 becomes "yes" and the logic of the flow diagram returns to box 404. If on the other hand, button switch 12 is pressed a second time before the expiration of the 3 second delay period, the answer to the question posed in box 412 is "yes" and the logic of the flow diagram proceeds through boxes 414, 416 and 418 to turn on the LED 14 and apply electrotransport current to the patient at a predetermined level for a predetermined (e.g., 10 minute) delivery interval. Once the drug delivery interval has expired, the answer to the question posed in box 418 becomes "yes" and the logic of the flow diagram proceeds through boxes 420, 422 and 424, which boxes increment the delivery count by one, turn off the LED 14 and stop the application of electrotransport current to the patient, respectively. Following box 424, the logic of the flow diagram returns to box 404.

The LED does not blink until after there has been two presses on button switch 12 within the short (e.g., three second) predetermined time period. Once the patient pushes button switch 12 two times within the three second delay period, the LED turns on and the predetermined drug delivery regimen is started. Once the drug delivery interval expires, the delivery count is augmented by one and both the LED and the drug delivery current are turned off. At this point (i.e., after the first drug delivery event has occurred), box 404 sets K equal to the delivery count, i.e., 1. Since K is no longer less than 1, the answer to the question posed in box 406 is "no" and box 426 causes the LED to blink one time, after which, K is reduced by 5 in box 428. Since K was only equal to 1 initially, following box 428, leaves K equal to a number less than 1. This causes the answer to the question posed in box 406 to become "yes" and the logic of the flow diagram cycles between boxes 406 and 408 until there is another push on button switch 12.

According to the above-described mode of operation, the LED is continuously turned on during the drug delivery interval when the device is applying current and delivering drug by electrotransport to the patient. During periods when there is no electrotransport drug delivery, the LED continuously cycles to periodically provide a blinking LED display which is indicative of the number of drug delivery events which have occurred (i.e., doses of drug administered by electrotransport). If there are no blinks of the LED, this signifies that there has not been any drug delivery event initiated by the patient. If there has been between one and five drug delivery events initiated by the patient, the LED blinks once during successive "blink displays". If there has been between six and ten drug delivery events initiated by the patient, the LED blinks two times during the successive blink displays. If there has been between eleven and fifteen drug delivery events, the LED blinks three times during successive blink displays, etc. Thus, in the predetermined regimen correlating the count to the number of on/off cycles of the LED, x equals 1 and y equals 5.

Most preferably, a delay (see box 430 in FIG. 4) is built in between the successive blink displays so as not to confuse the medical technician between the time a first blink display has ended and a subsequent blink display has begun. This delay can be anywhere on the order of about two to ten seconds or even longer.

As an alternative to the drug delivery history information being displayed automatically, the device may also be designed to operate in a mode whereby the dosing history is displayed only at the request of the patient or a medical technician. For example, the dosing history information can be displayed when button switch 12 is pressed only one time within the short (e.g., 3 second) predetermined time period discussed above. Given the overlap of functions relating to pushing button switch 12, the electronic circuitry connected to switch 12 must be capable of distinguishing between a patient requesting delivery of drug and medical personnel interrogating the event counter and storage apparatus.

Figure 3:
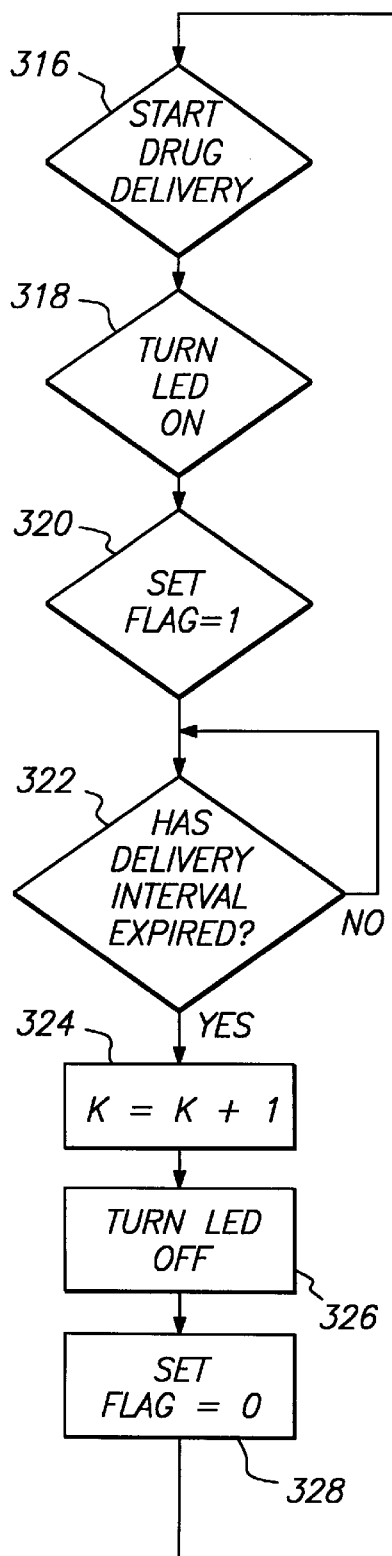
FIG. 3 is a flow diagram showing one example of logic for operation of the device illustrated in FIG. 2.
Figure 3:
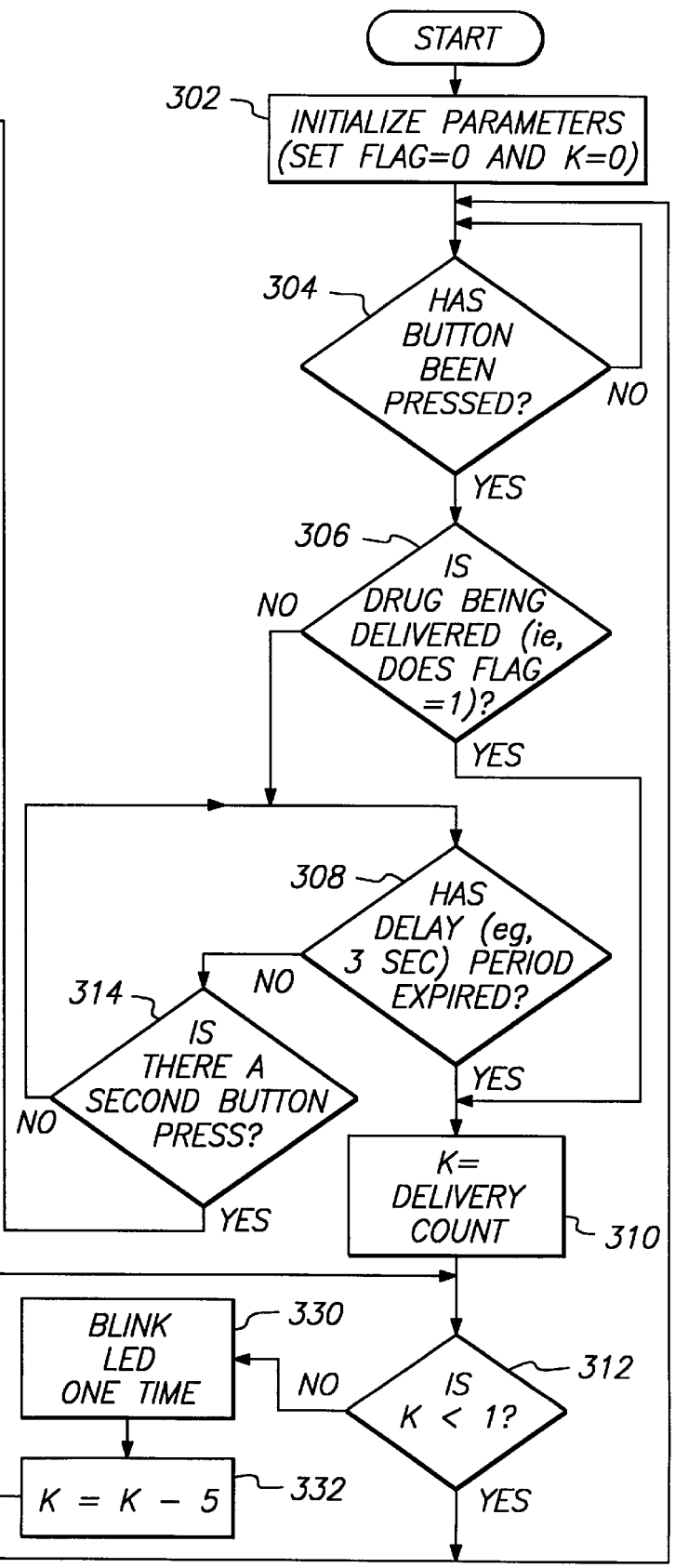

Referring now to FIG. 3, there is shown a mode of operation whereby the dosing history is displayed only at the request of the patient or a medical technician. In this mode of operation, pushing (i.e., closing) button switch 12 either initiates electrotransport drug delivery or initiates a display of the count (e.g., dosing history). Similar to the logic of the FIG. 4 flow diagram, the FIG. 3 flow diagram displays the dosing history information by blinking the LED according to a predetermined regimen. Similar to the FIG. 4 flow diagram, the initial step is to initialize certain system parameters (box 302) including setting both the flag count and K equal to zero. Following box 302, the logic of the flow diagram cycles at box 304 until button switch 12 is pressed, causing the logic to proceed to box 306.

If the device is not presently in a drug delivery interval (i.e., the device is not applying electrotransport current to the patient) then a three second time period begins. If no second press of button switch 12 occurs within the three second period, the answer to the question posed in box 308 becomes "yes" and the logic of the flow diagram proceeds to box 310 wherein a display of the recorded dosing history information is initiated. Since initially K is set equal to zero, the answer to the question posed in box 312 is "yes" and the logic of the flow diagram cycles back to box 304 without causing LED 14 to blink.

If on the other hand, there is a second press of push button 12 before the expiration of the 3 second delay period, the answer to the question posed in box 314 becomes "yes" and the logic of the flow diagram proceeds through boxes 316, 318 and 320, which boxes initiate application of electrotransport current, and hence drug delivery, to the patient, turn the LED on and set the flag equal to one, respectively. Once the predetermined (e.g., 10 minute) drug delivery interval has expired, the answer to the question posed in box 322 becomes "yes" and the logic of the flow diagram proceeds through boxes 324, 326 and 328, which boxes increment K by one, turn off the LED and reset the flag equal to zero, respectively. Following this, the logic of the flow diagram returns to box 304 and awaits a press of button switch 12. If the button switch 12 is then pressed only once within the 3 second delay period, the logic proceeds through box 310 in which the delivery count is set equal to K, which is now 1. Since K equals 1, the answer to the question posed in box 312 is "no" and the logic of the flow diagram proceeds through boxes 330 and 332, which boxes causes the LED to blink once and decrease K by 5, respectively. Box 332 causes the value of K to drop below 1, which in turn causes the answer to the question posed in box 312 to become "yes" and the logic proceeds back to box 304 where it cycles until push button switch 12 is again pressed.

As discussed in detail above, the display consists of blinking the LED according to a predetermined regimen. The LED blinks once for each 1 to 5 drug delivery events that have already occurred. If the patient has initiated no drug delivery events at the time the display of dosing history is initiated, then the LED will not blink at all. If the patient has previously initiated between one and five drug delivery events, the LED will blink once. If the patient has previously initiated between six and ten drug delivery events, the LED will blink twice. Thus, each blink of the LED signifies up to a predetermined number (e.g., up to five) drug delivery events which have previously been initiated by the patient. Those skilled in the art will appreciate that the particular predetermined numbers x and y chosen to correlate the number of blinks to the number of drug delivery events may be changed in accordance with the particular drug being delivered and particularly according to the expected number of drug delivery events likely to be initiated by the patient during the wearing period.

Those skilled in the art will also appreciate that the blinking of the LED may be accomplished either by blinking the LED on or by blinking the LED off, depending upon the initial state of the LED being unlit or lit, respectively. Thus, if the request for dosing history information is made when the device is currently delivering drug, and hence the LED is currently in a lit state, the blinking of the LED is accomplished by periodically turning the LED off. On the other hand, if the request for dosing history information is made at the time when the device is normally in an off mode, and hence the LED is in an unlit state, then the blinking of the LED is accomplished by periodically turning the LED on.

Alternatively, the blinking LED may be replaced with a beeper which beeps in accordance with a similar predetermined regimen described above in connection with the blinking LED. The logic flow of FIGS. 3 and 4 can be incorporated into the electronic circuitry on a electrotransport device in accordance with conventional circuit design principles. In addition to the modes of operation illustrated in FIGS. 3 and 4, the dosing history or other count information may be displayed in a manner which includes both an automatic display mode and a manually initiated display mode. For example, the electrotransport device 10 may operate by (i) automatically displaying the count during periods between active drug delivery intervals, similar to the mode of operation disclosed in FIG. 4, and (ii) displaying the count during the active drug delivery intervals by depressing push button switch 12. Preferably, the device has a "lock-out" feature during the drug delivery interval so that depressing push button switch 12 to initiate the display of the count does not (inadvertently) result in the initiation of another drug delivery interval.

Those skilled in the art of electrotransport drug delivery will readily appreciate that the device and method of the present invention may be used to count and display other events besides drug delivery dosing events. For example, the device of the present invention may include appropriate timing devices which measure either the elapsed wearing time for the device or the elapsed treatment time for the device. The device may then display the elapsed time by appropriately cycling the display between on and off states in order to indicate the number of hours and/or minutes which have elapsed. Alternatively, the device of the present invention may incorporate apparatus for sensing a patient condition and apparatus for comparing the sensed condition to a predetermined acceptable range. If the sensed condition is outside the predetermined range, the counter is incremented and the count later displayed to indicate to a medical technician the number of times when the patient's condition has fallen outside of the range. Examples of patient conditions which may be sensed and compared in this manner include breathing rate, blood glucose concentration, muscle movement (e.g., contraction), tissue oxygen content, tissue carbon dioxide content, body temperature, heart rate, or the like. The sensor provides a sense signal which is transmitted to a comparator which compares the sensed signal with a predetermined acceptable range for that signal. IF the signal is outside the predetermined range, the comparator signals the counter to increment the count by one. In this manner, the counter counts and stores the number of times when the patient's condition (e.g., heart rate) falls outside of a predetermined acceptable range. The count is then displayed either automatically or by appropriate means for interrogating the counter in order to inform a medical technician of the patient's history for that sensed condition. Knowing the number of such events which have occurred during the course of therapy, medical technicians can better adjust dosing rates and other parameters in order to more effectively treat the patient's medical condition.

While the present invention is not limited to any particular electrotransport device or to delivery of any particular drug by electrotransport, the invention has particular utility in those devices which allow the patient to self-administer drug. In this class of devices, self-administration of analgesic drugs to control pain represents an important segment.

Thus, the following example illustrates a preferred practice of the present invention. Those skilled in the art of electrotransport drug delivery will readily appreciate that the invention has much broader application than the specific example given hereinafter. The example is merely given to better illustrate the advantages which may be achieved in putting the invention to practice.

EXAMPLE

The fentanyl-containing donor reservoir is electrically connected to a silver anode and the electrolyte-containing counter reservoir is electrically connected to a silver/silver chloride cathode. The electrodes are in electrical contact, through conductive adhesive strips, with the outputs of the electronic circuit board assembly.

Each of the donor and counter hydrogel reservoirs has a nominal surface area of 2.75 $cm^2$ and a nominal cross sectional area of 0.15 $cm^2$. The anode donor reservoir contains about 1% to 2% of fentanyl HCl, approximately 30% polymers and additives including crosslinked polymers for hydrogel integrity, and optionally a humectant to inhibit water loss and enhance shelf stability. The anodic electrode is a silver foil laminated to a conductive adhesive. The anodic electrode surface area is about 2.30 $cm^2$.

The cathodic counter reservoir contains an electrolyte (e.g., NaCl) solution, optionally buffered, and approximately 30% polymers and additives including crosslinked polymers for hydrogel integrity, and optionally a humectant to inhibit water loss and fillers to enhance shelf stability.

The cathode electrode is a silver chloride material laminated to a conductive adhesive. The cathodic electrode surface area is about 2.30 $cm^2$.

The fentanyl delivery device is a single use, totally integrated electrotransport device substantially the same as the device 10' shown in FIG. 2. The device contains electronic circuitry, i.e., a printed circuit board assembly, a mechanical housing and drug-containing hydrogel donor reservoir and an electrolyte-containing counter reservoir for patient-controlled, on-demand administration of the narcotic analgesic fentanyl, in the form of fentanyl hydrochloride. The donor reservoir is anodic and the counter reservoir is cathodic. The system has a skin-compatible peripheral adhesive layer and is worn on the upper arm or chest for a 24-hour period.

The electronic circuitry, when activated by the patient, delivers a constant DC current to the electrode/reservoirs for a 10 minute drug delivery interval and allows up to six such delivery intervals per hour. Activation of the push button switch 12 is signalled to the patient by visual and/or audible signals.

Upon two successive presses of the button switch 12 within 3 seconds, the battery powered electronic circuitry delivers 240 $\mu A$ of DC current from the circuit board assembly to the two hydrogel reservoirs in contact with the patient's skin for the ten minute delivery interval. The output current is zero during periods between active drug delivery intervals (i.e., when the device is in an "off" mode). The battery is preferably a lithium coin type having a nominal open-circuit battery voltage of 3 volts. Upon completion of the ten minute delivery interval, the device automatically turns itself off and awaits another double press of the button switch 12 to initiate a subsequent drug delivery interval.

The count of drug doses delivered during the 24-hour active life of the device (or other defined earlier period) are displayed automatically when the device is in an "off" mode (i.e., when no drug is being delivered by electrotransport).

The count is presented in five unit increments between delivery intervals by cycling the LED between "on" and "off" (i.e., lit and unlit) states. In a preferred practice, the blinking of the LED (or the beeping of the beeper) is interpreted as follows: No blinking of the LED and/or no beeping of the beeper means no fentanyl delivery intervals have been initiated since the device has been worn by the patient. One blink of the LED and/or one beep of the beeper means that from 1 to 5 fentanyl delivery intervals have been initiated. Two blinks of the LED and/or two beeps of the beeper means that from 6 to 10 fentanyl delivery intervals have been initiated. N blinks of the LED and/or N beeps of the beeper means than from 5N−4 to 5N fentanyl delivery intervals have been initiated.

We claim:

1. A method of displaying how many events have occurred over a period of use of a patient-worn electrotransport delivery device by means of a delivery device display having on and off states, comprising:

counting the number of events which occur over the period of use and storing the count; and displaying the count by cycling the display between on and off states according to a predetermined regimen which correlates the number of on/off cycles to the count.

2. The method of claim 1, wherein the predetermined regimen correlates each on/off cycle of the display to between x and y events, x and y each being an integer from 0 to 100.

3. The method of claim 2, wherein zero on/off cycles of the display correlates to no events having occurred.

4. The method of claim 1, wherein the display is selected from the group consisting of a light having lit and unlit states, an audible alarm having sounding and no-sounding states, and a combination thereof.

5. The method of claim 4, wherein the light comprises a light emitting diode.

6. The method of claim 4, wherein the audible alarm comprises a beeper.

7. The method of claim 1, wherein the event comprises delivering drug by electrotransport during a delivery interval.

8. The method of claim 7, wherein the delivery interval is shorter than the period of use.

9. The method of claim 8, wherein the period of use is up to about 24 hours.

10. The method of claim 1, wherein the event comprises a patient condition which is sensed by the device.

11. The method of claim 10, including sensing and counting the number of times the patient condition falls outside a predetermined range.

12. The method of claim 1, wherein the event is manually initiated.

13. The method of claim 12, wherein at least some of the events are initiated by the patient activating a switch on the device.

14. The method of claim 1, wherein the display also displays when an event is occurring.

15. The method of claim 1, characterized by displaying the count between successive events.

16. The method of claim 1, characterized by manually initiating the display.

17. A patient-worn electrotransport delivery device, comprising:

a counter for counting the number of events which have occurred over a period of use and storing the count; and a display having on and off states, the display being operative to cycle between on and off states according to a predetermined regimen which correlates the number of on/off cycles to the count.

18. The device of claim 17, wherein the predetermined regimen correlates each on/off cycle of the display to between x and y events, x and y each being an integer from 0 to 100.

19. The device of claim 17 wherein zero on/off cycles of the display correlates to no events having occurred.

20. The device of claim 17, wherein the display is selected from the group consisting of a light having lit and unlit states, an audible alarm having sounding and no-sounding states, and a combination thereof.

21. The device of claim 20, wherein the light comprises a light emitting diode.

22. The device of claim 20, wherein the audible alarm comprises a beeper.

23. The device of claim 17, wherein the event comprises delivering drug by electrotransport during a drug delivery interval.

24. The device of claim 23, wherein the drug delivery is shorter than the period of use.

25. The device of claim 23, wherein the period of use is up to about 24 hours.

26. The device of claim 23, wherein the drug is an analgesic.

27. The device of claim 17, including a sensor for sensing a patient condition.

28. The device of claim 17, wherein each event comprises the sensed patient condition falling outside a predetermined range.

29. The device of claim 17, including a manually activated switch for initiating an event.

* * * * *